(12) United States Patent
Davis et al.

(10) Patent No.: US 6,630,320 B1
(45) Date of Patent: Oct. 7, 2003

(54) TREATMENT OF HYPERTENSION IN MAMMALS WITH HYDROLYZED WHEY PROTEINS

(75) Inventors: Martin E. Davis, Tonka Bay; Anand Rao, Savage, both of MN (US); Sylvie Gauthier; Yves Pouliot, both of Charny (CA)

(73) Assignee: Devisco Foods International, Inc., LeSueur, MN (US)

( * ) Notice: Subject to any disclaimer, the term of this patent is extended or adjusted under 35 U.S.C. 154(b) by 0 days.

(21) Appl. No.: 09/567,283

(22) Filed: May 8, 2000

(51) Int. Cl.$^7$ ................................................. C12Q 1/37
(52) U.S. Cl. ....................................................... 435/24
(58) Field of Search ........................... 424/400; 435/24

(56) References Cited

U.S. PATENT DOCUMENTS

| | | | |
|---|---|---|---|
| 3,857,966 A | 12/1974 | Feldman et al. | 426/7 |
| 3,932,672 A | 1/1976 | Pour-El et al. | 426/46 |
| 3,970,520 A | 7/1976 | Feldman et al. | 195/29 |
| 4,001,437 A | 1/1977 | Jaeggi et al. | 426/34 |
| 4,107,334 A | 8/1978 | Jolly | 426/7 |
| 4,154,675 A | 5/1979 | Jowett et al. | 210/33 |
| 4,218,490 A | 8/1980 | Phillips et al. | 426/549 |
| 4,293,571 A | 10/1981 | Olofsson et al. | 426/7 |
| 4,293,583 A | 10/1981 | Farr et al. | 426/657 |
| 4,427,658 A | 1/1984 | Maubois et al. | 424/177 |
| 4,482,574 A | 11/1984 | Lee | 426/7 |
| 4,486,413 A | 12/1984 | Wiesenberger et al. | 424/177 |
| 4,847,096 A | 7/1989 | Mellqvist et al. | 426/41 |
| 4,981,704 A | 1/1991 | Thibault | 426/41 |
| 5,039,532 A | 8/1991 | Jost et al. | 426/41 |
| 5,322,773 A | 6/1994 | Kaneko et al. | 435/68.1 |
| 5,369,015 A | 11/1994 | Yoshikawa et al. | 435/68.1 |
| 5,405,637 A | 4/1995 | Martinez et al. | 426/580 |
| 5,589,357 A | 12/1996 | Martinez et al. | 435/68.1 |
| 5,695,796 A | 12/1997 | Yamamoto et al. | 426/43 |
| 5,744,179 A | 4/1998 | Shimamura et al. | 426/41 |
| 5,854,029 A | 12/1998 | Yamamoto | 435/71.2 |
| 5,869,444 A | 2/1999 | Klein | 514/2 |
| 5,882,705 A | 3/1999 | Sato et al. | 426/41 |
| 5,952,193 A | 9/1999 | Shimamura et al. | 435/68.1 |

FOREIGN PATENT DOCUMENTS

| | | |
|---|---|---|
| EP | 0 474 506 | 3/1992 |
| JP | 04-082898 | 3/1992 |
| JP | 04282398 | * 10/1992 |
| JP | 04282400 | * 10/1992 |
| JP | 04-282400 | 10/1992 |
| JP | 06345664 | * 12/1994 |
| JP | 08-269088 | 10/1996 |
| WO | WO 99/65326 | 12/1999 |

OTHER PUBLICATIONS

Bachelard, H. and G. Drolet, Cardiovascular responses to paraventricular (PVN) injections of opioid agonists in conscious rats; *Abstract Society for Neuroscience*, 18: 1175; 1992. (Copy ordered).

Bachelard H. and M. Pitre, Regional haemodynamic effects of μ–, δ–, κ–opioid agonists microinjected into the hypothalmic paraventricular nuclei of conscious, unrestrained rats; Br. *J. Pharmacol*, 15:613–621, 1995. (Copy ordered).

Laragh; "L'hypertension"; *Recherche*, 105 (10): 1068–1076; Nov. 1979.

Pearce; "Whey Protein Recovery and Whey Protein Fractionation"; *Whey and Lactose Processing*, Zadow, J. G., ed.;271–316, London 1992.

Pitre, M., A. Nateau and H. Bachelard, Insulin sensitivity and hemodynamic responses to insulin in Wistar–Kyoto and spontaneously hypertensive rats, *Am. J. Physiol.* 271: E658–E668, 1996. (Copy ordered).

Pitre, M., H. Gaudreault, M. Santure, A Nadeau, and H. Bachelard; Isradipine and insulin sensitivity in hypertensive rats; *Am. J. Physiol.*, 39:E1038–E1048, 1999. (Copy ordered).

Bachelard, H., M. Pitre and A. Lessard; Mechanisms of the Regional Hemodynamic Effects of a μ–Opiod Receptor Agonist Microinjected into the Hyothalamic Paraventricular Nuclei of Conscious Unrestrained Rats; *JPET* 280:460–470, 1997.

Santuré, M. Pitre, N. Aaudreault, A. Marette, A. Nadeau and H. Bachelard; Effect of metformin on the vascular and glucose metabolic actions of insulin in hypertensive rats; *Am. J. Physio Gastrointest Liver Physiol* 278:G682–G692, 2000.

*Hawley's Condensed Chemical Dictionary*, Richard J. Lewis, Sr., 13th Edition, 937 (1997).

"Davisco Foods International, Advitech Solutions Join Forces to Produce Whey Protein Hydrolyzate",*Davisco Press Release* (1998).

Davisco "Nominated for Prestigious International Award for its Patented Hypertension–Reducing Whey Protein", *Davisco Press Release* (1999).

Abubakar et al., "Structural Analysis of New Antihypertensive Peptides Derived from Cheese Whey Protein by Proteinase K Digestion", *Journal of Dairy Science*, 81 3131–3138 (1996).

(List continued on next page.)

*Primary Examiner*—Alton Pryor
(74) *Attorney, Agent, or Firm*—Schwegman, Lundberg, Woessner & Kluth, P.A.

(57) ABSTRACT

Enzymatic digests of whey protein isolates were prepared using animal, bacterial and fungal proteases, and evaluated for antihypertensive activities. The antihypertension activity was obtained with a hydrolysate of whey protein isolate prepared with a porcine trypsin. The recovered hydrolysate is used to treat hypertension in mammals such as humans and domestic pets such as dogs and cats.

7 Claims, 4 Drawing Sheets

OTHER PUBLICATIONS

Abubakar et al. "New Derivation of the Inhibitory Activity Against Angiotensin Converting Enzyme (ACE) from Sweet Cheese Whey", *Tohoku Journal of Agricultural Research, 47* 1–8 (1996).

Cushman et al., "Spectrophotometric Assay and Properties of the Angiotensin–Converting Enzyme of Rabbit Lung", *Biochemical Pharmacology, 20* 1637–1648 (1971).

Ferreira et al., "Isolation of Bradykinin–Potentiating Peptides from *Bothrops jararaca* Venom", *Biochemistry, 9* 2583–2593 (1970).

Kohmura et al., "Inhibition of Angiotensin–Converting Enzyme by Synthetic Peptides of Human beta–Casein", *Agric. Biol. Chem., 53* 2107–2114 (1989).

Maruyama et al., "A Peptide Inhibitor of Angiotensin I Converting Enzyme in the Tryptic Hydrolysate of Casein", *Agric. Biol. Chem., 46* 1393–1394 (1982).

Maubois et al., "Les Peptides du Lait a Activite Physiologique III. Peptides du Lait a Effet Cardiovasculaire: Activities Antithrombotique et Antihypertensive", *Lait, 71* 249–255 (1991).

Mullally et al., "Identification of a Novel Angiotensin–I–Converting Enzyme Inhibitory Peptide Corresponding to a Tryptic Fragment of Bovine beta–Lactoglobulin", *FEBS Letters, 402* 99–101 (1997).

Oshima et al., "Peptide Inhibitors of Angiotensin I–Converting Enzyme in Digests of Gelatin by Bacterial Collagenase", *Biochemical et Biophysica Acta, 566* 128–137 (1979).

Takano, "Milk Derived Peptides and Hypertension Reduction", *Int. Dairy Journal, 8* 375–381 (1998).

Ju et al., "Effects of Limited Proteolysis on Gelation and Gel Properties of Whey Protein Isolate", *Journal of Dairy Science, 78*, 2119–2128 (1195).

Otte et al., "Effects of Limited Proteolysis on the Microstructure of Heat–Induced Whey Protein Gels at Varying pH", *Journal of Dairy Science, 79*, 782–790 (1996).

* cited by examiner

TREATMENT OF HYPERTENSION IN MAMMALS WITH HYDROLYZED WHEY PROTEINS

BACKGROUND OF THE INVENTION

The invention relates to a method for reducing hypertension in mammals with specific hydrolysates obtained by the enzymatic conversion of whey proteins.

Hypertension has been reported to be the most important cause of human deaths in industrialized countries. (See, for example, Laragh, J. H., 1979, *L'hypertension. Recherche,* 105 (10): 1068–1076) Nearly 30% of the fatalities among adults would result from hypertension or from its renal, coronary or neurological complications. The elucidation of the physiological mechanisms responsible for hypertension has lead to the introduction of several pharmaceuticals for the treatment of hypertension and/or its symptoms, which include increased heart rate and increased blood pressure.

It would be desirable to identify additional materials capable of treating hypertension or its symptoms, especially materials that can be easily employed as part of a simple regimen such as being included in food items.

BRIEF DESCRIPTION OF THE DRAWINGS

FIGS. 1–4 summarize the results of laboratory testing discussed in detail below.

SUMMARY OF THE INVENTION

It is an object of the invention to provide improvements in the field of treating hypertension in mammals.

It is an object of the invention to provide a method for reducing heart rate and blood pressure associated with hypertension in mammals.

These and other objects are accomplished by the invention by a mammalian treatment regimen entailing orally administration to humans or other mammals effective amounts of a hypertension-reducing composition obtained by: preparing an aqueous solution of whey protein isolate and a proteolytic enzyme; holding said solution under conditions effective to partially hydrolyze said whey protein isolate to provide a hydrolysate having the ability to reduce hypertension in mammals; and recovering said hydrolysate from said solution. The proteolytic enzyme is inactivated as necessary, preferably by heating. The hydrolysate is preferably dried for use in a regimen which comprises oral administration to a mammal, such as a human or a domestic pet such as a dog or cat, in amounts and at intervals effective to reduce hypertension in mammals. Many of the preferred aspects of the invention are described below.

DETAILED DESCRIPTION OF THE INVENTION

Whey protein isolates (WPI) can be obtained from commercial-scale fractionation of cheese whey by various processes, including ion-exchange processing using cationic and/or anionic resins selected for the intended functionality of the isolate. (Pearce, R. J., 1992, Whey protein recovery and whey protein fractionation, *Whey and Lactose Processing*, J G Zadow, Ed., Elsevier, London, 271–316.) Commercial WPI products issued from ion-exchange processing, such as BiPRO™ (Davisco Foods International, Inc., LeSueur, Minn.), are characterized by a high protein content (>94% w/w), low ash content (<3%), traces (<1%) of fat and lactose. The protein distribution of a typical WPI shows 55–65% β-lactoglobulin, 17–25% α-lactalbumin, 4–7% bovine serum albumin, 7–11% immunoglobulins and less than 1% others.

BiPRO™ whey protein isolate is the preferred source of whey protein isolate for use in the invention and is available from Davisco Foods International, Inc., with offices at 11000 W. 78th Street, Suite 210, Eden Prairie, Minn. 55344. The preferred BiPRO™ whey protein isolate has a (PDCAAS) Protein Digestibility Corrected Amino Acid Score of 1.14. The fat and lactose levels are less than 1%. The BiPRO™ whey protein isolate is prepared by ion-exchange technology, and contains about 55–65% (w/w) β-lactoglobulin. Preferaby, the whey protein isolate employed according to the invention will contain at least 55% and preferably at least 60% β-lactoglobulin, with the remaining comprising α-lactalbumin, serum albumin and immunoglobulins in the above ranges. BiPRO™ is essentially undenatured and is fully soluble over the pH range 2.0 to 9.0, and has the following analysis:

| Analysis* | Specification | Typical Range | Test Method |
|---|---|---|---|
| Moisture (%) | 5.0 max. | 4.9 ± 0.1 | Vacuum Oven |
| Protein, dry basis (N x 6.38)(%) | 95.0 min. | 97.8 ± 0.4 | Combustion |
| Fat (%) | 1.0 max. | 0.3 ± 0.1 | Mojonnier |
| Ash (%) | 3.0 max. | 2.0 ± 0.3 | Gravimetric |
| Lactose (%) | 1.0 max. | <0.5 | by difference |
| pH | 6.7–7.5 | 7.0 ± 0.1 | 10% Sol. @ 20° C. |

-continued

| Analysis* | Specification | Typical Range | Test Method |
|---|---|---|---|

*All results reported "AS IS" basis except where noted. Standard Methods for the Examination of Dairy Products, 16th Edition.

As noted, whey protein isolates other than BiPRO™ can be employed and where used preferably have similar analyses to that above, varying by from 0 to 25%, e.g. from 5 to 10%, or less, from the above Typical Range values. A suitable whey protein isolate can be produced having similar properties through a selective ion exchange process that selects the primary functional proteins—beta—lactoglobulin and alpha—lactalbumin—for concentration and spray drying. Such a process is described in U. S. Pat. No. 4,154,675 to Jowett, et al., and U.S. Pat. No. 4,218,490 to Phillips, et al. If properly produced, whey protein fractions having lower protein contents, e.g., as low as 35%, might be employed. In addition, β-lg produced by ion exchange separation can also be employed, but is less preferred than the BiPRO™ whey protein isolate.

On a more detailed analysis of BiPRO™ whey protein isolate, the following is found or each 100 grams of whey protein isolate:

| Component | |
|---|---|
| Calories | 374 |
| Calories From Total Fat | 3 |
| Total Fat (g) | 0.3 |
| Saturated Fat (g) | 0.2 |
| Cholesterol (mg) | 10 |
| Sodium (mg) | 600 |
| Potassium (mg) | 120 |
| Total Carbohydrates (g) | 0 |
| Dietary Fiber (g) | 0 |
| Sugars (g) | 0 |
| Protein (g) | 93 |
| Vitamin A (IU) | 20 |
| Vitamin C (mg) | 2.0 |
| Calcium (mg) | 120 |
| Iron (mg) | 5 |
| Phosphorus (mg) | 25 |
| Magnesium (mg) | 15 |
| Ash (g) | 2 |
| Moisture (g) | 5 |

And, to provide an amino acid profile of the preferred BiPRO™ whey protein isolate, samples were subjected to drying for 24 hours in a dessicator over phosphorus pentoxide and sodium hydroxide. The dry samples were hydrolyzed in HCl vapor (6N HCl with 1% phenol and 0.5% sodium sulfite) under Argon atmosphere. After 20 hours of hydrolysis at 110 degrees Celsius, the samples were dissolved in 200 µl of Beckman Na-S sample buffer. This acid hydrolysis method destroys tryptophan.

Analyses were conducted on a Beckman 6300 Amino Acid Analyzer. Norleucine was used as an internal standard. The analysis showed the following:

| | Grams Amino Acid Per | |
|---|---|---|
| Amino Acid | 100 g protein | 100 g powder |
| Alanine | 7.6 | 7.01 |
| Arginine | 2.0 | 1.84 |
| Aspartate | 10.1 | 9.31 |
| Cysteine/Cystine | 4.3 | 3.96 |
| Glutamine | 14.3 | 13.18 |
| Histidine | 1.6 | 1.48 |
| Isoleucine* | 5.4 | 4.98 |
| Leucine* | 13.7 | 12.63 |
| Lysine* | 9.6 | 8.85 |
| Methionine* | 2.4 | 2.21 |
| Phenylalanine* | 3.1 | 2.86 |
| Proline | 4.5 | 4.14 |
| Serine | 4.90 | 4.52 |
| Threonine* | 5.30 | 4.89 |
| Tyrosine | 2.90 | 2.67 |
| Valine* | 5.60 | 5.16 |
| Totals | 100.10 | 92.29 |

*Essential Amino Acids

Again, when whey protein isolates other than BiPRO™ are employed, they preferably have similar analyses to that above, varying by from 0 to 25%, e.g., from 5–10%, or less, from the above values.

Enzymatic digests of BiPRO™ whey protein isolate were prepared using animal, bacterial and fungal proteases, in order to determine the potential of these commercial substrates for the preparation of peptide mixtures having antihypertensive activities. The main objective of the present study was to investigate the antihypertensive effect of some specific whey protein hydrolysates. The following summarizes experiments that have been carried out in conscious spontaneously hypertensive rats (SHR) to characterize the antihypertensive effect and establish the dose response curve for each hydrolysate. The SHR are considered as a genetic model of essential hypertension and are currently used to understand the development and establishment of hypertension and to determine the blood pressure lowering effect of newly synthesized antihypertensive drugs. Moreover, in a previous study carried out in SHR, we found that the intravenous injection of an angiotensin I-coverting enzyme (ACE) inhibitor, Captopril, caused a marked reduction in blood pressure accompanied by significant vasodilations in renal, superior mesenteric and hindquarter vascular beds (unpublished data). Therefore, the SHR appears to be very reactive to ACE inhibition and then should provide us with very useful information in determining if specific whey protein hydrolysates exhibit a significant antihypertensive property.

Three whey protein hydrolysates (namely, 601, 603K and 605K) and controls phosphate buffered saline (PBS) and untreated BiPRO™ whey protein isolate, have been examined. The effects of each whey protein on mean and phasic arterial blood pressure and heart rate have been investigated in conscious unrestrained male SHR. In the present study, the animals were chronically instrumented with one intravascular catheter implanted in the left femoral artery to permit a continuous recording of blood pressure and heart rate. This technique is very well developed in our laboratory and is routinely performed (Bachelard, H. and G. Drolet, Cardiovascular responses to paraventricular (PVN) injections of opioid agonists in conscious rats, *Abstract Society for Neuroscience.* 18: 1175,1992; Bachelard, H. and M. Pitre, Regional haemodynarnic effects of µ-, δ-, κ-opioid agonists microinjected into the hypothalamic paraventricular nuclei of conscious, unrestrained rats, Br. *J. Pharmacol,*

115: 613–621, 1995; Pitre, M., H. Gaudreault, M. Santure, A. Nadeau, and H. Bachelard. Isradipine and insulin sensitivity in hypertensive rats, *Am. J Physiol.*, 39: E1038–E1048, 1999; Pitre, M., A. Nateau and H. Bachelard, Insulin sensitivity and hemodynamic responses to insulin in Wistar-Kyoto and spontaneously hypertensive rats, *Am. J Physiol.* 271: E658–E668, 1996). This experimental approach constitutes a powerful tool to investigate the hemodynamic responses to whey proteins in conscious rats. The non-invasive technique currently used by others to measure systolic blood pressure, the tail cuff sphygmomanometer, is stressfull for the animal, (the rat has to be immobilized in a restrainer during measurement), and is subject to a large variability. Therefore, considering the inherent variability in blood pressure measurements in conscious animals, and that the SHR rats are known to be very reactive to stressful stimuli, we believed that there is some incertitude in measurements made with the tail cuff technique, particularly in establishing a steady baseline measurement. In contrast, by directly and continuously recording blood pressure, it is easier to take into account this variability and make more reliable blood pressure measurements. Moreover, our rats were well adapted to the system for a few days prior to the experiments, and direct measurement of blood pressure was made without causing any pain or stress to the animal. Therefore, the direct and continuous recording of blood pressure and heart rate in conscious, unrestrained animals represent a clear advantage over the other non-invasive technique.

Materials and Methods

Whey protein isolate (BiPRO™) was obtained from Davisco Foods International (Le Sueur, Minn., USA). HEPES Sodium salt, Hippuryl-L-Histidyl-L-Leucine, and Angiotensin Converting Enzyme (from rabbit lung) were purchased from Sigma Chemical Co. (St. Louis, USA). All other products used were analytical grade.

Whey proteins (BiPRO™) were solubilized at 20% W/V, adjusted to pH 8.0 or 8.5 by using a mixture of NaOH and KOH 4N and maintained at temperatures between 40° C. and 50° C. corresponding to the optimal temperature of the enzymes used. Table 1 reports the characteristics of the enzymes used for the preparation of the enzymatic hydrolysates for the study. BiPRO™ whey protein isolate was utilized for the preparation of 601, 603K and 605K. The protein solutions were incubated with the proteases at an enzyme: substrate ratio of 1:800 for 601, 1:50 for 603K and 1:100 for 605K. The enzymatic hydrolysis was performed under pH-stat conditions until a degree of hydrolysis (DH) of 4.5–6.5% for 601 and under a combination of pH-stat and osmometry methods until a DH of 7.0–10.0% for 603K, and a DH of 13.0–17.0% for 605K. The hydrolysis reaction was stopped at the selected DH values by means of heat treatment (75 to 85° C. for 15 s) in a plate heat exchanger to inactivate the enzyme and followed by cooling and storage at 5–10° C. until further processing. The resulting hydrolysates were further spray dried and handled as powdered ingredient. Fractions can be taken based on molecular weight and tested for relative activity, with the most active fractions selected.

A typical analysis for the 601K and 603K products prepared from BiPRO™ whey protein hydrolysate are given below.

| Analysis* (601) | Specification | Typical Range | Test Method |
|---|---|---|---|
| Moisture (%) | 5.0 max. | 4.0 ± 0.5 | Vacuum Oven |
| Total Nitrogen (TN), % | 14.1 min. | | Combustion |
| Protein dry basis (N × 6.38)(%) | 90.0 min. | 91.0 ± 0.5 | Calculated |
| Amino Nitrogen (AN), % | 1.7 min. | | Formol Titration |
| AN/TN | 12.0 min. | 12.0–15.0 | Calculated |
| Degree of Hydrolysis, % | 5.0 min. | 5.5–6.5 | OPA Method |
| Fat (%) | 1.0 max | <1.0 | Mojonnier |
| Ash (%) | 6.0 max. | 5.5 ± 0.3 | Standard** |
| Lactose (%) | 1.0 max. | <1.0 | by difference |
| pH | 8.5 max. | 8.0 ± 0.2 | 10% Sol. @ 20° C. |

| Molecular Weight Profile (HPLC) Range (Daltons) | Soluble Peptides*** |
|---|---|
| >10,000 | 50–60% |
| 5,000–10,000 | 10–20% |
| 2000–5000 | 10–20% |
| <2000 | 10–20% |

*All results reported "AS IS" basis except where noted.
**Standard Methods for the Examination of Dairy Products, 16th Edition.
***Percent of total soluble peptides in 0.45 μ filtrate.

| Analysis* (603K) | Specification | Typical Range | Test Method |
|---|---|---|---|
| Moisture (%) | 5.0 max. | 4.0 ± 0.5 | Vacuum Oven |
| Total Nitrogen (TN), % | 14.1 min. | | Combustion |
| Protein, dry basis (N × 6.38) % | 94.0 min. | 95.0 ± 0.5 | Calculated |
| Amino Nitrogen (AN), % | 2.2 min. | 2.4 ± 0.2 | Formol Titration |
| AN/TN, % | 15.8 min. | 16.3 ± 0.5 | Calculated |
| Degree of Hydrolysis, % | 7.0 min. | 7–10 | OPA Method |
| Fat (%) | 1.0 max. | <1.0 | Mojonnier |
| Ash (%) | 5.0 max. | 3.5 ± 0.3 | Gravimetric |
| Lactose (%) | 1.0 max. | <1.0 | by difference |
| pH | 7.5 max. | 7.0 ± 0.2 | 10% Sol. @ 20° C. |
| Scorched Particles | 15 mg/25 g max. | 7.5 mg | ADPI |

| Molecular Weight Profile (HPLC) | | |
|---|---|---|
| | Range (Daltons) | Peptides |
| | >10,000 | 25–35% |
| | 5000–10,000 | 10–20% |
| | 2000–5000 | 25–35% |
| | <2000 | 20–30% |

TABLE 1

Characteristics of the enzyme sources used for the preparation of hydrolysates

| Enzyme (Name, Supplier) | Source | Optimal pH | Temp. (° C.) | Hydrolysate |
|---|---|---|---|---|
| Trypsin VI Trypsin Activity 2,400 U/mg minimum Chymotrypsin activity 350 U/mg minimum Canadian Innovatech Inc Abbotsford, BC, Canada | Porcine | 8.0 | 37 | 601 |
| Protease P Amano-6 Proteinase activity 60,000 units/g minimum Amano, Enzyme Co. Ltd | Fungal | 7.5 | 45 | 605K |

TABLE 1-continued

Characteristics of the enzyme sources used for the preparation of hydrolysates

| Enzyme (Name, Supplier) | Source | Optimal pH | Temp. (° C.) | Hydrolysate |
|---|---|---|---|---|
| Lombard, IL, USA Multifect Activity 3,000 GSU/ml minimum (Note: GSU is Genencor Subtlisin Units---developed internally by Genencor) Genencor International Rochester, NY, USA | Bacterial | 8.5 | 50 | 603K |

Determination of Antihypertension Activity—Methods

All surgical and experimental procedures followed institutional animal care guidelines. Male SHR rats (aged 20 to 24 weeks and weighing 300–350 g) were purchased from Charles River Canada. The rats were anesthetized with a mixture of ketamine-xylazine (100 and 10 mg kg$^{-1}$), respectively, i.p., supplemented as required) and one catheter was implanted in the distal abdominal aorta via the left femoral artery (for measurement of blood pressure and heart rate). Then, the catheter was tunneled subcutaneously to emerge at the back of the neck and was passed through a flexible, protecting spring attached to a custom-made harness worn by the rat. The rats were given s.c. injections of Ampicillin (150 mg kg$^{-1}$) and Anafen (5mg kg$^{-1}$) and returned to their home cages. Experiments began at least 4 days after this surgical step.

Throughout the experiments, three variables were recorded (heart rate and phasic and mean arterial blood pressure) using a Biopac Data Acquisition and Analysis system (Model MP 100, AcqKowledge software version 3.1). At selected time points heart rate, phasic and mean arterial blood pressure were measured, to represent the full profile of the effects of the hydrolysates or BiPRO whey protein isolate, and related to the pre-treatment baseline value. The rats were conscious, unrestrained and were allowed free access to water and food for the duration of the experiment.

Experimental Protocol

The cardiovascular changes elicited by oral administration of BiPRO whey protein isolate or specific whey protein hydrolysates (601, 603K, 605K) have been evaluated in conscious, unrestrained SHR. The rats were used on four consecutive days, during which they received increasing doses of only one specific hydrolysate (601, 603K, 605K) or the BiPRO by gastric intubation. The lyophilized whey protein hydrolysate powder was dissolved in 0.2 mM PBS (pH 7.2) (the same vehicle, 0.2 mM PBS, was used for control administrations) and was given in a volume of 0.5 ml. All solutions were freshly prepared. Thus, on a typical day, soon after basal measurements of blood pressure and heart rate, the rats were given the vehicle (control PBS on day 1) or an isolated dose of a specific hydrolysate (30 mg/kg on day 2, 75 mg/kg on day 3 and 150 mglkg on day 4) or BiPRO whey protein isolate (30 mg/kg on day 2, 75 mg/kg on day 3 and 150 mg/kg on day 4). The blood pressure and heart rate effects of a single oral administration of PBS, BiPRO whey protein isolate or the whey protein hydrolysate was evaluated over a period of 7 hours.

Results

Resting values for cardiovascular variables measured every morning before any intervention during four consecutive days are shown in Table 2. As we can see, there was no significant difference between the basal mean arterial blood pressuire and heart rate values measured on days 1, 2, 3 and 4.

TABLE 2

Baseline values of heart rate (HR) and mean arterial blood pressure (MAP) in conscious, unrestrained SHR rats.

| Treatment | Weight, g | Age, Week | Day | HR (bpm) | MAP (mmHg) |
|---|---|---|---|---|---|
| Vehicle (PBS) N = 36 | 322 ± 4 | 24.1 ± 0.2 | 1 | 311 ± 6 | 173 ± 3 |
| #601 (30 mg/kg$^{-1}$) N = 9 | 321 ± 9 | 23.2 ± 0.5 | 2 | 308 ± 8 | 174 ± 6 |
| #601 (75 mg/kg$^{-1}$) N = 8 | 317 ± 9 | 23.4 ± 0.6 | 3 | 320 ± 13 | 179 ± 4 |
| #601 (150 mg/kg$^{-1}$) N = 7 | 313 ± 10 | 23.0 ± 0.5 | 4 | 305 ± 19 | 175 ± 9 |
| #603K (30 mg/kg$^{-1}$) N = 10 | 315 ± 7 | 23.7 ± 0.2 | 2 | 301 ± 10 | 168 ± 7 |
| #603K (75 mg/kg$^{-1}$) N = 10 | 315 ± 7 | 23.7 ± 0.2 | 3 | 304 ± 9 | 167 ± 5 |
| #603K (150 mg/kg$^{-1}$) N = 10 | 315 ± 7 | 23.7 ± 0.2 | 4 | 292 ± 11 | 164 ± 5 |
| #605K (30 mg/kg$^{-1}$) N = 8 | 321 ± 6 | 24.0 ± 0.0 | 2 | 290 ± 9 | 170 ± 5 |
| #605K (75 mg/kg$^{-1}$) N = 8 | 321 ± 6 | 24.0 ± 0.0 | 3 | 296 ± 14 | 176 ± 9 |
| #605K (150 mg/kg$^{-1}$) N = 8 | 321 ± 6 | 24.0 ± 0.0 | 4 | 299 ± 13 | 163 ± 6 |
| BiPRO (30 mg/kg$^{-1}$) N = 8 | 328 ± 5 | 25.5 ± 0.2 | 2 | 299 ± 9 | 182 ± 5 |
| BiPRO (75 mg/kg$^{-1}$) N = 8 | 328 ± 5 | 25.5+0.2 | 3 | 300 ± 11 | 179 ± 6 |
| BiPRO (150 mg/kg$^{-1}$) N = 8 | 328 ± 5 | 25.5 ± 0.2 | 4 | 290 ± 6 | 168 ± 7 |

Values are means±SEM; n is the number of rats. (Groups represent those used to assess blood pressure and heart rate effects of single oral administration of vehicle (PBS), 601, 603K, 605K or BiPRO whey protein isolate in conscious, unrestrained SHR. MAP, mean arterial blood pressure; HR, heart rate; bpm, beats per minute.

Cardiovascular Responses to Hydrolysate 601

Figure 1:
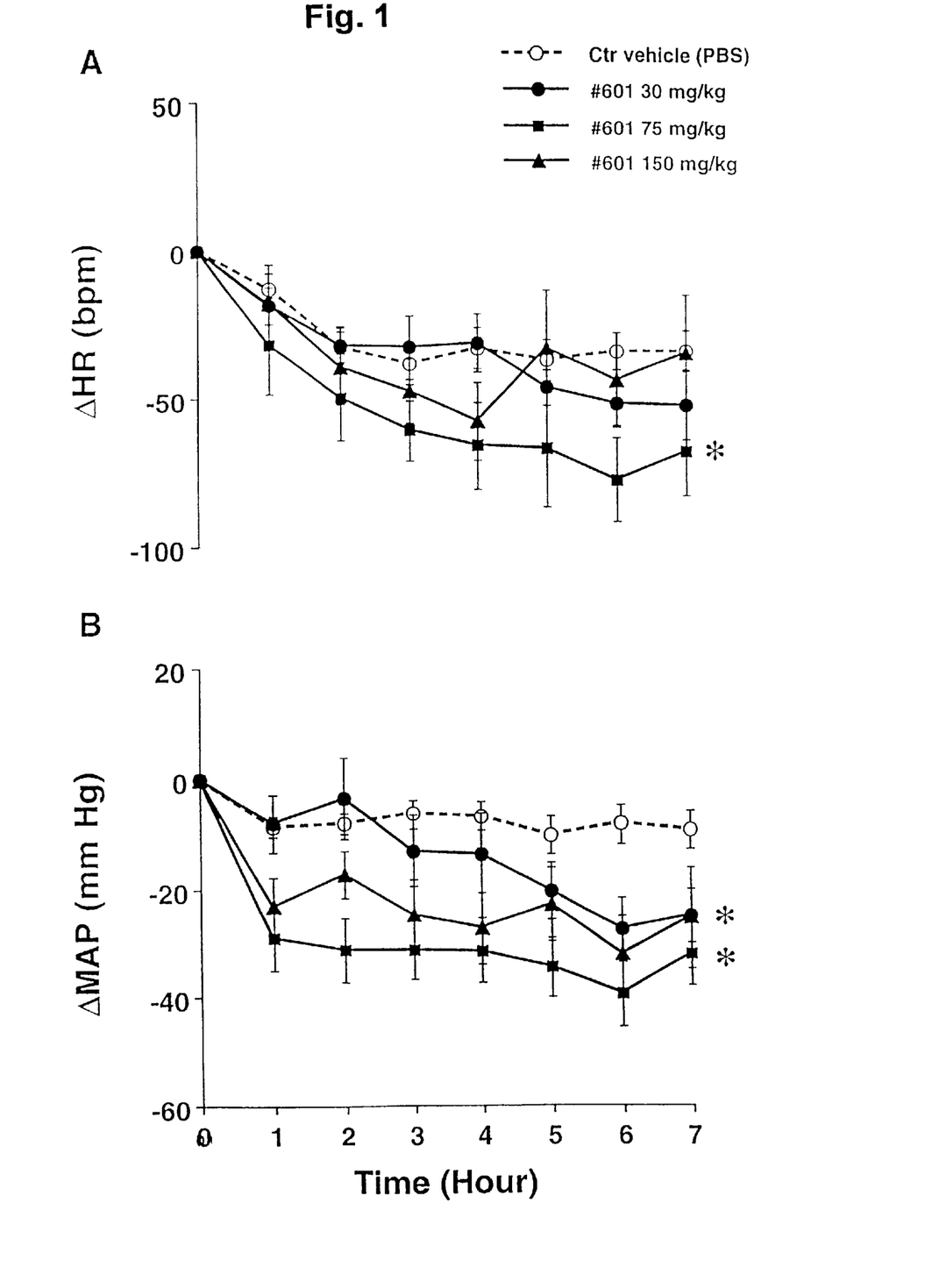
FIG. 1. Changes in heart rate (A) and mean arterial blood pressure (B) elicited by single oral administration (time 0) of vehicle (0.2 mM PBS pH 7.2;O, n=36 rats) or 601 at the dose of 30 (n=9 rats), 75 (n=8) or 150 mg/kg (n=7) in conscious, unrestrained spontaneously hypertensive rats (SHR). Each point indicates the mean with standard errors shown by vertical lines. *P<0.05 versus vehicle-treated group, ANOVA followed by Fisher's test. HR, heart rate; bpm, beats per minute; MAP, mean arterial blood pressure.

FIG. 1 shows the changes in heart rate and mean arterial blood pressure after oral administration of 0.5 ml of 0.2 mM PBS (n=36) or hydrolysate 601 at doses of 30 (n=9), 75 (n=8) or 150 mg/kg (n=7) in conscious, unrestrained spontaneously hypertensive rats (SHR). Each point indicates the mean with standard errors shown by vertical lines. *$P<0.05$ versus vehicle-treated group, ANOVA followed by Fisher's test. HR, heart rate; bpm, beats per minute; MAP, mean arterial blood pressure. Except for the 75 mg/kg dose, which elicited a significant (at 4,6 and 7 h) decrease in heart rate (maximum of −77±14 bpm at 6 h), we found no significant difference between the heart rate responses elicited by intra-gastric administration of PBS and hydrolysate 601 at the doses of 30 and 150 mg/kg. However, we observed a significant reduction in mean arterial blood pressure following intra-gastric administration of the different doses of hydrolysate 601 when compared to control administration of PBS.

Thus, at the dose of 30 mg/kg we observed a significant hypotensive effect (−27±6 mm Hg) 6 hours after administration of the hydrolysate. At the dose of 75 mg/kg of hydrolysate we observed a marked and long-lasting hypotensive effect (significant at 1–7 h) when compared with the effects of control administration of PBS. The maximum decrease in mean arterial blood pressure (−39±6 mm Hg) was achieved 6 h after the administration. A similar hypotensive effect was also observed following the intra-gastric administration of 150 mg/kg of the hydrolysate (significant at 1 and 3–7 h). The maximum decrease in mean arterial blood pressure (−32±7 mm Hg) was achieved 6 h after the administration.

Figure 2:
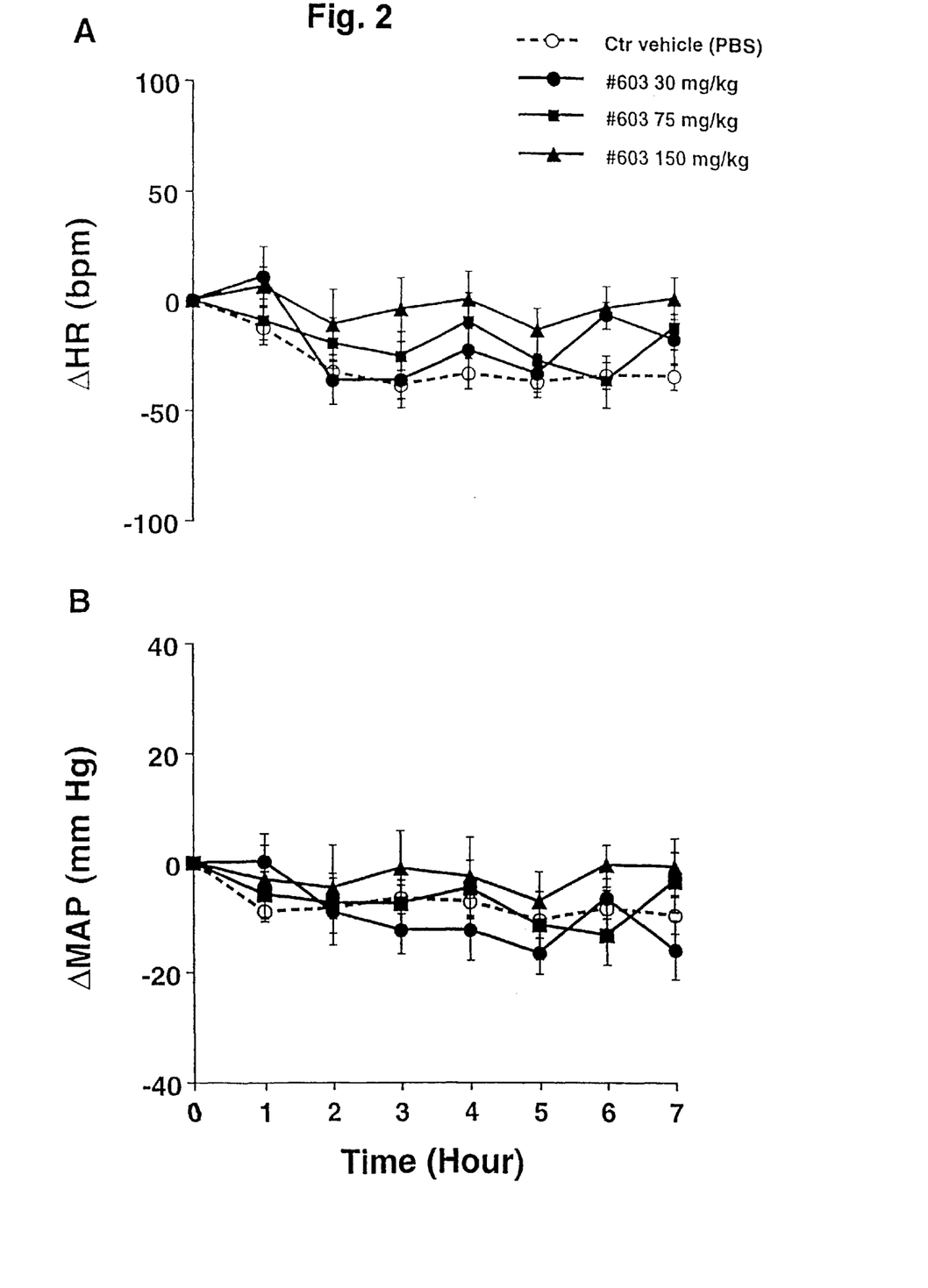
FIG. 2. Changes in heart rate (A) and mean arterial blood pressure (B) elicited by single oral administration (time 0) of vehicle (0.2 mM PBS pH 7.2;O, n=36 rats) or 603K at the dose of 30 (n=10 rats), 75 (n=10) or 150 mg/kg (n=10) in conscious, unrestrained spontaneously hypertensive rats (SHR). Each point indicates the mean with standard errors shown by vertical lines. *P<0.05 versus vehicle-treated group, ANOVA followed by Fisher's test. HR, heart rate; bpm, beats per minute; MAP, mean arterial blood pressure.
Figure 3:
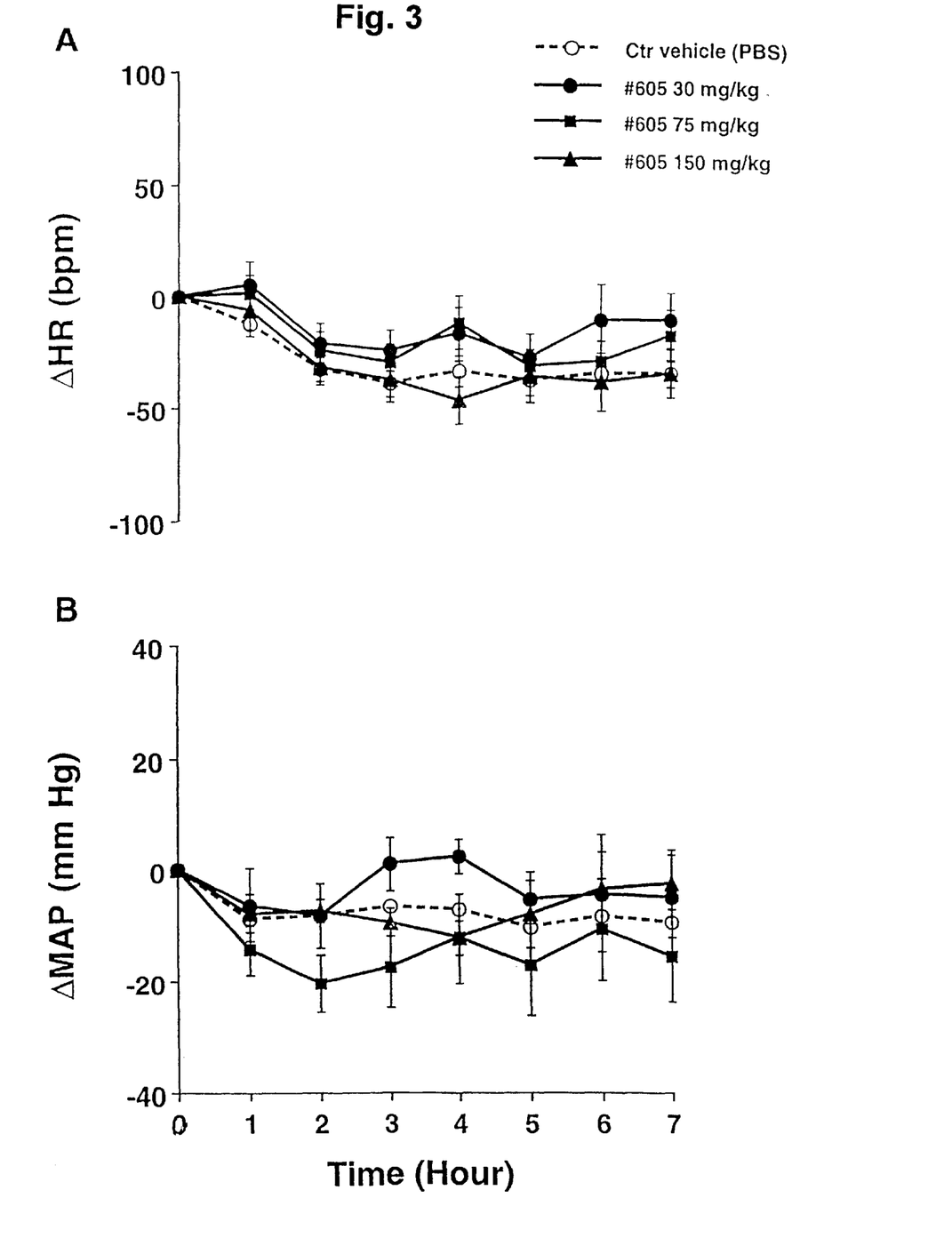
FIG. 3. Changes in heart rate (A) and mean arterial blood pressure (B) elicited by single oral administration (time 0) of vehicle (0.2 mM PBS pH 7.2; O, n=36 rats) or 605K at the dose of 30 (n=8 rats), 75 (n=8) or 150 mg/kg (n=8) in conscious, unrestrained spontaneously hypertensive rats (SHR). Each point indicates the mean with standard errors shown by vertical lines. HR, heart rate; bpm, beats per minute; MAP, mean arterial blood pressure.
Figure 4:
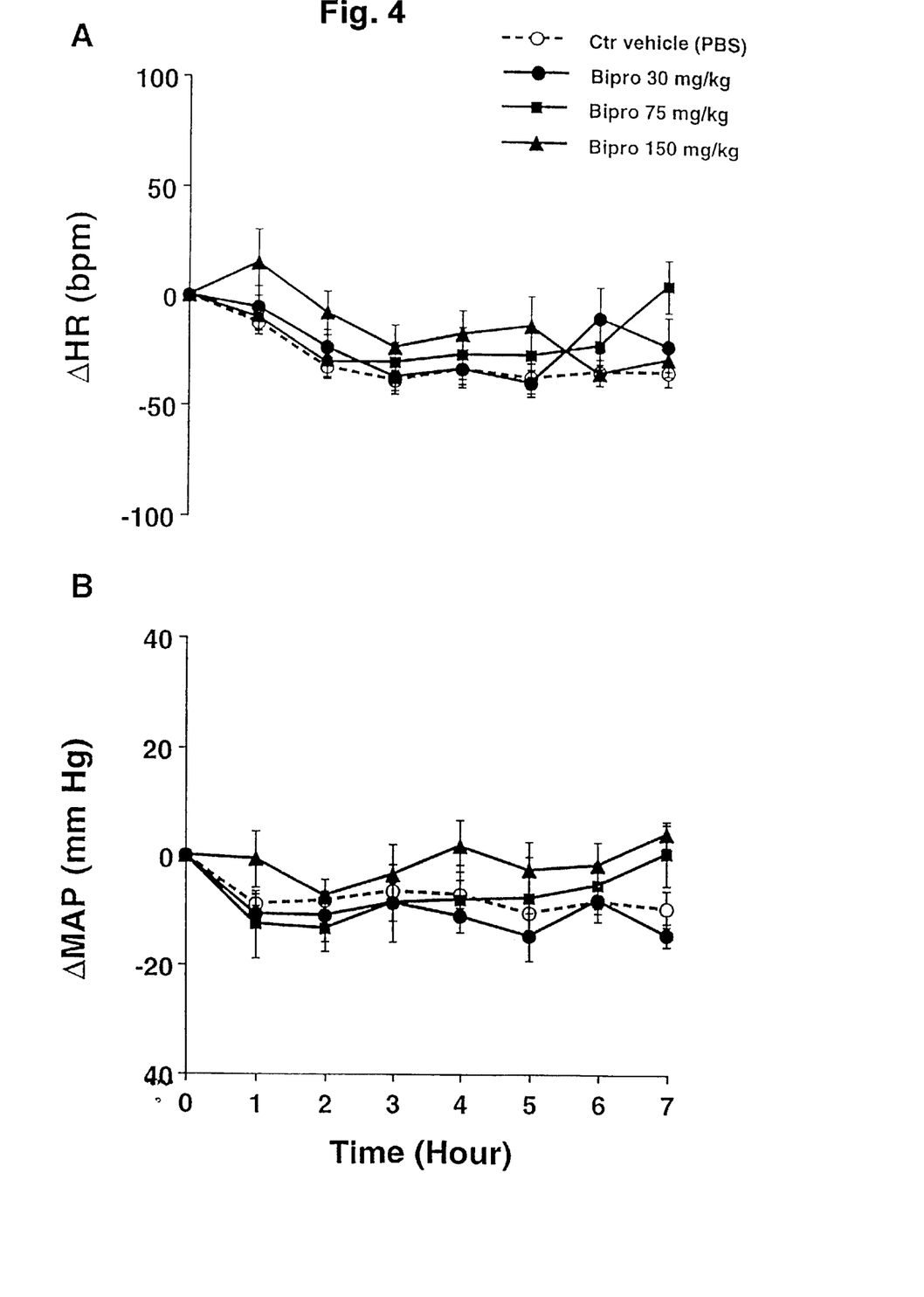
FIG. 4. Changes in heart rate (A) and mean arterial blood pressure (B) elicited by single oral administration (time 0) of vehicle (0.2 mM PBS pH 7.2; O, n=36 rats) or BiPRO at the dose of 30 (n=8 rats), 75 (n=8) or 150 mg/kg (n=8) in conscious, unrestrained spontaneously hypertensive rats (SHR). Each point indicates the mean with standard errors shown by vertical lines. HR, heart rate; bpm, beats per minute; MAP, mean arterial blood pressure.

Cardiovascular Responses to BiPRO and Hydrolysate 603K, 605K FIGS. 2–4 show the changes in heart rate and mean arterial blood pressure after oral administration of 0.5 ml of 0.2 mM PBS (n=36) or hydrolysate 603K (FIG. 2) or 605K (FIG. 3) or BiPRO whey protein isolate (FIG. 4) at doses of 30, 75, or 150 mg/kg. We found no significant difference between the heart rate or mean arterial blood pressure responses elicited by intra-gastric administration of PBS and hydrolysate 603K or 605K or BiPRO whey protein isolate at the different doses tested.

Conclusions

The present results indicate that:

Single oral administration of hydrolysate 601 (at the doses of 75 or 150 mg/kg) in conscious unrestrained SHR significantly reduced mean arterial blood pressure from 1 to 7 hours after administration.

Blood pressure returned to the initial level at 24 hours after administration.

Conversely, the hydrolysate 603K and 605K and the control BiPRO whey protein isolate (at any of the doses tested) did not change the mean arterial blood pressure of the SHR rats in this study.

A suitable regimen for treatment with the noted hydrolysate 601 will comprise oral administration of the above doses of 75 to 150 mg/kg at intervals of from 2 to 24 hours. More broadly, the dosages and intervals could be increased or decreased by from 50 to 500 percent, as might be indicated by treatment over time.

The above description is intended to enable the person skilled in the art to practice the invention. It is not intended to detail all of the possible modifications and variations which will become apparent to the skilled worker upon reading the description. It is intended, however, that all such modifications and variations be included within the scope of the invention which is seen in the above description and otherwise defined by the following claims. The claims are meant to cover the indicated elements and steps in any arrangement or sequence which is effective to meet the objectives intended for the invention, unless the context specifically indicates the contrary.

What is claimed is:

1. A treatment regimen for a mammal to reduce symptoms of hypertension, said regimen comprising:

orally administering to the mammal, a whey protein hydrolysate prepared by treatment of a whey protein isolate with trypsin, in amounts and at intervals effective to reduce symptoms of hypertension, wherein the hydrolysate has molecular weight profiles within the ranges

| (Daltons) | soluble peptides |
|---|---|
| >10,000 | 50–60% |
| 5,000–10,000 | 10–20% |
| 2000–5000 | 10–20% |
| <2000 | 10–20%. |

2. A treatment according to claim 1, wherein the hydrolysate is prepared from a whey protein isolate characterized as follows:

| Analysis | Range |
|---|---|
| Moisture (%) | 4.7 ± 0.2 |
| Protein, dry basis | 97.5 ± 1.0 |
| Fat (%) | 0.6 ± 0.2 |
| Ash (%) | 1.7 ± 0.3 |
| Lactose (%) | <0.5 |
| pH | 7.0 ± 0.2. |

3. A treatment according to claim 2 wherein trypsin employed in the hydrolysis comprises trypsin from mammal, poultry or fish sources.

4. A treatment according to claim 2 wherein trypsin employed in the hydrolysis comprises porcine trypsin.

5. A treatment according to claim 1, wherein the hydrolysate has a degree of hydrolysis of from 3 to 20%.

6. A treatment according to claim 1, wherein the hydrolysate will be orally administered at a dose of 75 to 150 mg/kg at intervals of from 2 to 24 hours.

7. A treatment regimen for a mammal to reduce symptoms of hypertension, said regimen comprising:

orally administering to the mammal, a whey protein hydrolysate prepared by treatment of a whey protein isolate with a proteolytic enzyme, in amounts and at intervals effective to reduce symptoms of hypertension, wherein the hydrolysate is prepared from a whey protein isolate characterized as follows:

| Analysis | Range |
|---|---|
| Moisture (%) | 4.7 ± 0.2 |
| Protein, dry basis | 97.5 ± 1.0 |
| Fat (%) | 0.6 ± 0.2 |
| Ash (%) | 1.7 ± 0.3 |
| Lactose (%) | <0.5 |
| pH | 7.0 ± 0.2 | wherein the hydrolysate has molecular weight profiles within the ranges

| (Daltons) | soluble peptides |
|---|---|
| >10,000 | 50–60% |
| 5,000–10,000 | 10–20% |
| 2000–5000 | 10–20% |
| <2000 | 10–20%. |

* * * * *